(12) United States Patent
Branch et al.

(10) Patent No.: US 6,248,515 B1
(45) Date of Patent: Jun. 19, 2001

(54) METHODS FOR THE EARLY DETECTION OF HIV INFECTION

(76) Inventors: Donald R. Branch, 67 College Street, Toronto, Ontario (CA), M5G 2M1; David J. Phipps, 525 University Ave., Suite 925, Toronto, Ontario (CA), M5G 2L3

( * ) Notice: Subject to any disclaimer, the term of this patent is extended or adjusted under 35 U.S.C. 154(b) by 0 days.

(21) Appl. No.: 09/351,666

(22) Filed: Jul. 13, 1999

Related U.S. Application Data

(63) Continuation of application No. 08/699,339, filed on Aug. 19, 1996.
(60) Provisional application No. 60/008,207, filed on Dec. 5, 1995.

(51) Int. Cl.[7] ............................. C12Q 1/70; A61K 39/42; A61K 39/21; C07K 16/00
(52) U.S. Cl. ..................... 435/5; 424/160.1; 424/208.1; 530/388.35
(58) Field of Search ..................... 435/5; 424/160.1, 424/208.1; 530/388.35

(56) References Cited

U.S. PATENT DOCUMENTS

| 5,565,319 | 10/1996 | Pedersen et al. | 435/5 |
| 5,648,209 | 7/1997 | Avrameas et al. | 435/5 |
| 5,688,637 | 11/1997 | Moncany | 435/6 |

OTHER PUBLICATIONS

Baron T. et al. "Detection of bovine immunodeficiency–like virus infection in experimentally infected calves," *Arch. Virol.*, 143:181–189 (1998).

Brickell P.M. "The pp60c–src family of prtein tyrosine kinases: structure, regulation and function," *Crit. Rev. Oncogenesis* 3:401–446 (1992).

Busch M.P. "Time course of detection of viral and serologic markers preceding human immunodeficiency virus type 1 seroconversion: implications for screening of blood and tissue donors," *Transfusion*, 35; 91–97 (1995).

Cayota a., et al. "Defective protein tyrosine phosphorylation and altered levels of p59fyn and p56lck in CD4 T cells from HIV infected patients," *Int. Immuno.* 6:611–621 (1994).

Chow LM et al., "Negative regulation of T–cell receptor signalling by tyrosine protein kinase p50csk," *Nature 365*; 156 (1992).

Cohen D.I. et al. "Participation of tyorsine phosphorylation in th ecyctopathic effect of human immunodeficiency virus–1," *Science* 256:542–544(1992).

Hirai N. et al. "Detection of antibodies against bovine immunodeficiency–like virus in daily cattle in Hokkaido" *J. Vet. Med. Sci.* 58:455–527.

Hivroz C. et al. "Human immunodeficiency virus gp120 and derived peptides activate protein tyrosine kniase p56ick in human CD4 lymphocytes," *Eur. J. Immunol.* 23; 600–607 (1993).

Horak I.D. et al. "No T cell tyrosine protein kinase signalling or calcium mobilization after CD4 association with HIV–1 o r HIV–1 gp120," *Nature*, 3348; 557–560. (1990).

(List continued on next page.)

Primary Examiner—Hankyel T. Park
(74) Attorney, Agent, or Firm—Lahive & Cockfield; Siulio A. DeConti, Jr.; Elizabeth A. Hanley

(57) ABSTRACT

Methods for the early detection of HIV infection by detecting a change in signal transduction mediator activity, particularly, an enzyme mediator, more particularly a member of the src protein tyrosine kinase family. The methods are applicable to HIV detection with serum, plasma, blood cell lysates, urine and saliva media. The methods provide a very early, reliable, specific and sensitive test of seronegative HIV infection that is affordable and practical on a large scale.

10 Claims, 4 Drawing Sheets

OTHER PUBLICATIONS

Imamoto A et al., "Disruption of the csk gene, encoding a negative regulator of Src family tyrosine kinases, leads to neural tube defects and embryonic lethality in mice," *Cell* 73:1117–1124 (1993).

Juszczak R.J. et al."Effect of human immunodeficiency virus gp120 glycoprotein on the association of the protein tyrosine kinase p56lck with CD4 in human T lymphocytes," *J.Biol.Chem.* 266; 11176–11183 (1991).

Kashiwase H. et al. "Characterization of one monoclonal antibody against feline immundeficiency virus p24 and its applciaiton to antigen capture," ELISA. *J. Virol. Meth.* 68:183–192 (1997).

Kaufmann R. et al. "The HIV–1 surface protein gp120 has no effect on transmembrane signal transduction in T cells," *J.Aids* 15:760–770 . (1992).*

Malik R. et al. "Prevalences of feline leukemia virus and feline immunodeficiency virus infections in cats in Sydney. Aust.," *Vet. J.* 75:323–327 (1997).*

Orloff G.M. et al. "hiv–1 binding to CD4 T cells does not induce a Ca2+ influx or lead to activation of protein tyrosine knases," *Aids Res.Hum.Retrov.* 7; 587–593 (1991).*

Otsyula M.G. et al. "Immunoassay for the detection of simian immunodeficieny virus and human immunodeficieny virus in serum," *Lab. Animal Sci.* 46:198–201 (1996).*

Perelson A.S. et al. "HIV dynamics in vivo: viral clearnace rate, infected cell life span and viral generation time," *Science* 271:1582–1586 (1996).*

Petersen L. R. et al."Duration to time from onset of human immunodeficiency virus type 1 infectiousness to development of detectable antibody," *Transfusion*, 34; 283–289 (1994).*

Phipps, D.J. et al. "An octapeptide analogue of HIV gp120 modulates protein tyrosine kinase activity in activated peripheral blood lymphocytes," *Clin. Exp. Immunol.* 100; 412–418 (1995).*

Sibille P. et al. "Comparison of serological tests for the diagnosis of felive immunodeficiency virus infection of cats," *Vet. Microbiol.*, 45:259–27 (1995).*

Wei X. et al. "Viral dynamics in human immunodeficiency virus type–1 infection," *Nature* 373:117–122 (1995).*

Zhang S. et al. "Detection of bovine imunodeficiency virus antibodies in cattle by western blot assay with recombinant gag protein," *J. Vet. Diag. Invest.* 9:347–351 (1997).*

* cited by examiner

METHODS FOR THE EARLY DETECTION OF HIV INFECTION

This application is a continuation application of Ser. No. 08/699,339 filed on Aug. 19, 1996, Pending. The contents of all of the aforementioned application are hereby incorporated by reference and also claims the benefit of Provisional No. 60/008,207 filed Dec. 5, 1995.

FIELD OF THE INVENTION

This invention relates to methods for the early detection of HIV by the determination of a change in signal transduction mediator activity, particularly protein tyrosine kinase activity.

BACKGROUND TO THE INVENTION

Currently, infection with HIV is usually diagnosed by the detection of HIV specific antibodies in serum using either ELISA or Western Blot. Prior to development of HIV-specific antibodies, there exists a "window period" of seronegative HIV infection wherein an individual is infected with HIV but is not detected as HIV positive using standard ELISA or Western Blot assay. In one study, this window period has averaged 45 days from the date of infection, with 90% seroconverting within 141 days while 10% of individuals did not seroconvert for up to 6 months (1). Recent improvements in anti-HIV antibody detection systems have reduced the window period of seroconversion to approximately 22 days after infection. However, this estimate included a large 95% CV ranging from 10–34 days (2). One Canadian judicial report stated that "The greatest contributor to residual risk of HIV transmission (by transfusion) is the window period during which donors are infected but have not developed antibodies to a detectable level" (3).

Although every unit of donated blood for transfusion purposes is tested for HIV specific antibodies, the window period puts the safety of the blood supply in jeopardy since a person with seronegative HIV infection could donate a unit of HIV infected blood without being detected. Due to this small, but significant risk, the blood collection facilities screen donors to minimize donations from individuals considered to be at risk for HIV infection. Current estimates of the rate of transfusion related HIV infection from seronegative units of blood vary from 1:36,000 (4) to 1:60,000 (5) to 1:153,000 (6) to 1:250,000 (3). There were a total of 1,1418,916 units of untreated blood components transfused in 1993–1994 in Canada, including plasma, apheresis platelets, single donor platelets, red blood cells and cryoprecipitated AHF (7). Therefore, in Canada alone, the number of HIV infections resulting from transfusions of HIV infected, seronegative blood donations in 1993–1994 could be as low as 6 or as high as 39. Since blood products from individual donations are pooled, a single unit of HIV infected, antibody negative blood could potentially contaminate multiple components. If transfusion infected individuals do not have cause to seek HIV testing, they will spread HIV through intravenous drug use, sexual contacts or maternal-fetal transmission. The numbers of potential infections arising from these individuals during their 10–12 year asymptomatic period of HIV infection cannot be calculated.

The Western Blot and ELISA antibody tests currently in use to screen donated units for the presence of HIV do not detect seronegative HIV infections. Three test kits which are not antibody based are currently commercially available and can detect seronegative HIV infection. Both the quantitative competitive polymerase chain reaction (QC-PCR) marketed by Roche Ltd. and the branch chain DNA (bDNA) marketed by Chiron Corp. detect HIV-specific RNA in plasma of patients infected with HIV. These kits capture HIV RNA from plasma or serum and use different amplification systems to amplify the small amount of RNA present to a measurable signal (8). However, the above two test kit procedures have significant limitations. Both QC-PCR and bDNA cost approximately $100 (USD) per test sample. Neither test kit is currently approved by Health and Welfare Canada for HIV diagnosis in Canada. In two U.S. test sites, bDNA detected only 69% and 75% of HIV antibody positive, asymptomatic patients. (8).

An ELISA test for HIV p24 antigen detects serum p24 antigen and reduces the window period of HIV detection to 18–22 days after infection (2). Although this test has been adopted by the blood industry in both Canada and the United States, the efficacy of this test and its minor reduction in the length of the window period, does not outweigh its financial burden on the public.

Therefore, there remains a need for a reliable, specific and sensitive test of seronegative HIV infection that is affordable and practical on a large scale.

It has been demonstrated that HIV infection of either peripheral blood lymphocytes or the cell line, Jurkat, with HIV, results in enhanced levels of phosphotyrosine containing proteins 4–5 days following infection (9). Levels of phosphotyrosine on two proteins (pp95 and pp55) were increased 30 minutes after exposure of Jurkat to Jurkat transfected with gp120 (a model of syncytia formation, cells were not infected with HIV). Levels of phosphotyrosine containing proteins declined 4 hours after exposure.

It has been reported that of asymptomatic HIV infected patients (average CD4=295 cells/$\mu$l), 7/25 had elevated fyn protein and decreased lck protein. In addition, there was no change demonstrated in levels of phosphotyrosine in the resting T lymphocytes from patients infected with HIV (9).

Juszczak et al have demonstrated that gp120 and gp120-derived peptides transiently induced tyrosine phosphorylation and activation of $p56^{lck}$ in normal, resting peripheral blood lymphocytes and a T lymphocyte cell line, HUT 78 (12). Levels of phosphotyrosine and lck activity rose at 5 minutes, peaked at 15 minutes and returned to control levels 30 minutes following treatment.

Horak et al have demonstrated that treatment of activated T lymphocyte clones with either gp120 or HIV did not alter levels of phosphotyrosine containing proteins or activity of $p56^{lck}$ when treated for 0.5–15 min.(13).

Hivroz et al have demonstrated that gp120 and gp120-derived peptides transiently induce tyrosine phosophorylation and activation of lck in normal, resting peripheral blood lymphocytes and in a T lymphocyte cell line HUT 78 (14). Levels of phosophotyrosine and lck activity rise at 5 minutes, peak at 15 minutes and return to control levels 30 minutes after treatment with either gp120 or gp120-derived peptides.

Kaufmann et al demonstrated that treating resting peripheral blood lymphocytes with gp 120 for 1 hour did not induce a change in levels of phosphotyrosine containing proteins, intracellular calcium, protein kinase C (a serine/threonine protein kinase) or arachidonic acid metabolites (15).

Orloff et al have demonstrated that infecting normal, resting peripheral blood lymphocytes and activated lymphocyte blasts with HIV does not alter levels of phosphotyrosine or activity of $p56^{lck}$ for 1–120 minutes after infection (16).

Phipps et al have demonstrated that gp120-derived peptides transiently reduce the activity of lck but transiently enhance the activity of fyn and src in activated peripheral blood lymphocyte blasts (17).

Current kinase assays present significant problems. Standard in vitro immune complex kinase assays are not amenable to the screening of numerous samples due to their complex, multi-step procedure and are only semi-quantitative using densitometric analysis of autoradiographs. They also suffer from the same two drawbacks as existing quantitative kinase assays.

The UBI quantitative PTK (protein tyrosine kinase) assay kit currently available relies on immunoprecipitated PTK-mediated tyrosine phosophorylation of synthetic amino acid peptide substrates. Immunoprecipitated PTK is incubated with the peptide and $\gamma^{32}$P-ATP, the reaction stopped and an aliquot of kinase mixture transferred to filter discs, washed, dried and the degree of phosphorylation determined by liquid scintillation counting. The kit can distinguish between different families of PTK but not between different members of the same family. The Pierce quantitative PTK or PKC ELISA-based colorimetric assay binds a biotinylated tyrosine-containing peptide to avidin-treated 8-well microtitre strips. PTK-containing immunoprecipitates are added to phosphorylate the peptides, residual proteins washed out, HRP-labelled anti-phosphotyrosine added, residual antibody washed out, HRP substrate added and the resulting color that is generated is quantified against a standard phosphotyrosine-containing peptide, spectrophotometrically. The kit cannot distinguish between different PTK.

The two major disadvantages of existing kinase assays are:
1) the need to extensively process blood in order to isolate a target cell population; and
2) the lack of standardization of immunoprecipitation.
1) Current density gradient-based techniques for the isolation of peripheral blood mononuclear cells PBMC from whole blood require a) the extensive handling of biohazardous material; b) the need to transfer samples to new processing tubes at least three times prior to immunoprecipitation, which increases the risk of mixing up samples; c) the extensive washing of cells to remove the residual density gradient media and risking the loss of the sample; d) the enhanced cost of density gradient medium and blood processing.
2) Investigators currently conjugate anti-PTK to protein A-sepharose (or similar solid matrix material) to prepare immune conjugates used to immunoprecipitate PTK from cell lysates. Protein A-sepharose is a slurry of microscopic beads that require washing of both immunoconjugates and immunoprecipitates prior to processing. Washing and aspiration of waste supernatants enhances processing time and increases the risk of loss of sample which can result in the application of different amounts of immunoprecipitate to the kinase reaction enhancing inter-test variability.

REFERENCE LIST

The present specification refers to the following publications, each of which is expressly incorporated herein by reference.

1. Petersen L. R., Satten G. A., Dodd R., Busch M., Gleinman S., Grindon A., Lenes B. and the HIV Seroconversion Study Group (1994). Duration to time from onset of human immunodeficiency virus type 1 infectiousness to development of detectable antibody. Transfusion 34; 283–289.
2. Busch M. P., Lee L. L. L., Satten G. A., Henrard D. R., Farzadegan H., Nelson K. E., Read S., Dodd R. Y. and Peterson L. R. (1995). Time course of detection of viral and serologic markers preceding human immunodeficiency virus type 1 seroconversion: implications for screening of blood and tissue donors. Transfusion 35; 91–97.
3. Mr. Justice Horace Krever, Interim Report, "Commission of Inquiry on the Blood System in Canada", Chapter 4.
4. Donahue J. G., Nelson K. E., Munoz A., McAllister H. A., Yawn D. H., Ness P. M. and Cohen N. D. (1990). Transmission of HIV by transfusion of screened blood. N. Engl. J. Med. 323, 1709.
5. Nelson K. E., Donahue J. G., Munoz A., Cohen N. D., Ness P. M., Teague A., Stambolis V. A., Yawn D. H., Callicott B., McAllister H. et al (1992). Annal. Intern. Med. 117; 554–559.
6. Cumming P. D., Wallace E. L., Schorr J. B., and Dodd R. Y. (1989). Exposure of patients to human immunodeficiency virus through the transfusion of blood components that test antibody negative. N.Engl. J. Med. 321; 941–946.
7. CRCS Blood Services Statistical Report 1993–1994.
8. Cao Y, Ho D. D., Todd J., Kokka R., Urdea M., Lifson J. D., Piatak M., Chen S., Hahn B. H., Saag M. S. and Shaw G. M. (1995). Clinical evaluation of branched chain DNA signal amplification for quantifying HIV type 1 in human plasma. Aids Res. Hum. Retrov. 11; 353–361.
9. Cayota a., Vuilller F., Siciliano J. and Dighiero G. (1994). Defective protein tyrosine phosphorylation and altered levels of p59$^{fyn}$ and p56$^{lck}$ in CD4 T cells from HIV infected patients. Int. Immuno. 6: 611–621.
10. Bickell P. M. (1992). The pp60$^{c-etc}$ family of protein-tyrosine kinases: structure, regulation and function. Crit. Rev. Oncogenesis 3: 401–446.
11. Cohen D. I., Tani Y., Tian H., Boone E., Samelson L. E. and Lane H. C. (1992). Participation of tyrosine phosphorylation in the cytophatic effect of human immunodeficiency virus-1. Science 256; 542–544.
12. Juszczak R. J., Turchin H., Truneh A., Culp J., Kassis S. (1991). Effect of human immunodeficiency virus gp120 glycoprotein on the association of the protein tyrosine kinase p56$^{lck}$ with CD4 in human T lymphocytes. J.Biol.Chem. 266; 11176–11183.
13. Horak I. D., Popovic M., Horak E. M., Lucas P. J., Gress R. E., June C. H., Bolen J. B. (1990). No T cell tyrosine protein kinase signalling or calcium mobilization after CD4 association with HIV-1 or HIV-1 gp120. Nature, 3348; 557–560.
14. Hivroz C., Mazerolles F., Soula M., Fagard R., Graton S., Meloche S., Sekaly R. P., Fischer A. (1993). Human immunodeficiency virus gp120 and derived peptides activate protein tyrosine kinase p56$^{lck}$ in human CD4 T lymphocytes. Eur. J. Immunol. 23; 600–607.
15. Kaufmann R., Laroche D., Buchner K., Hucho F., Rudd c., Lindschau C., Ludgwig P. Hoer A., Oberdisse E., Kopp J., Korner I. J., Repke H. (1992). The HIV-1 surface protein gp120 has no effect on transmembrane signal transduction in T cells. J.Aids 15; 760–770.
16. Orloff G. M., Kennedy M. S., Dason C., McDougal J. S. (1991) hiv-1 binding to CD4 T cells does not induce a Ca$^{2+}$ influx or lead to activation of protein tyrosine kinases. Aids Res.Hum.Retrov. 7; 587–593.
17. David J.Phipps, Penelope Reed-Doob, Douglas K. MacFadden, John P. Piovesan, Gordon B. Mills, Donald R. Branch (1995). An octapeptide analogue of HIV gp120 modulates protein tyrosine kinase activity in activated peripheral blood lymphocytes. Clin. Exp. Immunol. 100; 412–418.
18. Wei X, Ghosh S. K., Taylor M. E., Johnson V. A., Emini E. A., Deutsch P., Lifson J. D., Bonhoeffer S., Navak M.

A., Hahn B. H., Saag M. S., Shaw G. M. (1995). Viral dynamics in human immunodeficiency virus type-1 infection. Nature (1995), 373: 117–122.
19. Perelson A. S., Neumann A. U., Markavitz M., Leonard J. M., Hudd (1996). HIV dynamics in vivo:virian clearance rate, infected cell life-span, and viral generation time. Science, 271: 1582–1586.

SUMMARY OF THE INVENTION

It is an object of the present invention to provide a new diagnostic and quantitative assay for the very early detection of HIV, which assay overcomes the aforesaid limitations of prior art methods.

Accordingly, in its broadest aspect the invention provides a method for the early detection of HIV infection comprising detecting a change in signal transduction mediator activity or level relative to an HIV uninfected population standard.

By the term "signal transduction mediator" as used in this specification, is meant a molecule involved in transducing signals from the surface of a cell to the nucleus which results in activation of the cell as measured by gene transcription, protein production and expression, cell proliferation or chemotaxis, liberation of effector molecules, phagocytosis or expression of effector functions. Signal transduction mediators include, enzymes such as kinases and phosphatases.

A change in activity of an enzyme signal transduction mediator is defined as an increase or a decrease in the rate of catalytic function of that enzyme compared as to the average catalytic function of the enzyme in the unaffected control population.

A change in level of an enzyme signal transduction mediator is defined as an increase or a decrease in the absolute level or quantity of the enzyme compared to the average levels of the enzyme in the unaffected control population.

The method of the invention is preferably applicable to the detection of the change in activity or level under the influence of HIV of tyrosine kinase, serine-threonine kinase and tyrosine-serine-threonine-kinase and more particularly to members of the Src protein tyrosine kinase family, namely Src, yes, fyn ($p59^{fyn}$),lck ($p56^{lck}$), lyn, fgr, hck, blk and yrk; and the csk protein tyrosine kinase family, namely, csk and ctk (also known as lsk or ntk).

The method of the invention is also applicable to the detection of the change in activity or level under the influence of HIV of protein tyrosine phosphatase, in particular CD45-associated phosphatase and SHP-1.

The methods of the invention are applicable to detection with body fluids, including, but not limited to serum, plasma blood cell lysates, urine or saliva media. In this specification and claims, blood cell lysate is included in the definition of body fluid, notwithstanding it is actually prepared from blood cells present in a body fluid.

The present invention, preferably, relates to the regulation of src-family protein tyrosine kinases which are enzymes involved in cellular, including T lymphocyte activation. Surprisingly, we have found that HIV antibody positive, asymptomatic patients have levels of $p59^{fyn}$ kinase activity 12 times that of HIV negative controls despite a decrease in the amount of $p59^{fyn}$ protein in these patients as compared to uninfected controls. The FYN kinase activity in the plasma of these patients is also increased compared to uninfected controls. When cells are infected with HIV in vitro, levels of kinase activity increase within 30 minutes of infection. These kinetics of induction of kinase activitiy identify this as an early response of the cell to infection with HIV. Without being bound by theory, we believe that activity of the src-family protein tyrosine kinase $p59^{fyn}$ is elevated in the lymphocytes of individuals infected with HIV regardless of their serostatus. The use of in vitro immune complex kinase assays to detect protein tyrosine kinase activation identifies individuals with seronegative HIV infection. Since protein tyrosine kinase activation is a response to infection with HIV at the cellular level, kinase activity will be elevated in peripheral blood as soon as HIV infection becomes systemic, corresponding to the acute retroviral syndrome.

The use of this procedure as a screening tool for HIV infection decreases the window period of detection of HIV infection to a matter of days.

We have found that kinase activity did not change in patients infected with either hepatitis B (n=6), hepatitis C (n=7) viruses, CMV (n=5) or in uninfected controls (n=34). This data is consistent with the hypothesis that elevated kinase activity is a specific response to infection with HIV.

Cohen et al (11) have demonstrated that cells infected with HIV in vitro had elevated levels of phosphotyrosine, the outcome of activated PTKs. In this reference, activity was not examined in vivo, nor was there any examination of the effect of HIV infection on the activity of discrete PTKs.

Current methods to detect HIV seronegative infection detect HIV RNA in plasma. The detection of activated protein tyrosine kinases in lymphocytes will be independent of the amount of HIV in plasma or serum and is not related technically or intellectually with QC-PCR or bDNA. Current detection of HIV-specific antibody uses ELISA and/or Western Blot techniques and can only identify seropositive HIV infections. Neither of these techniques are related to activated protein tyrosine kinases in lymphocytes.

The quantitative kinase assays of use in the present invention overcome the prior art assay limitations. Density gradient media is not necessary since PBMC separated in Vacutainer PCT tubes can be used or a whole blood lysate can be used or plasma/serum can be used. Both quantitative kinase assays described herein use anti-PTK antibody conjugated directly to a macroscopic bead or to a well in a 96-well microtitre plate. These antibodies are prepared in standardized lots and cannot be washed off during immunoprecipitation and thus, prevent inter-test variability. In addition, they are simple procedures that are amenable to a screening test due to having fewer steps than existing kinase assays.

The methods of use in the practice of the invention are applicable to not only early detection of seronegative HIV infection, but also asymptomatic infection after seroconversion wherein anti-HIV antibodies are present.

While the preferred methods of the invention detect an increase in activity or level of the signal transduction mediator following HIV infection, the present invention includes methods which detect a decrease in activity or level of the mediator.

The PTK csk is known to down regulate the kinase activity of all src-family PTK by phosphorylating the C-terminal negative regulatory tyrosine (Chow L M et al (1992) Nature 365; 156; Imamoto A and Sopiano P (1993) Cell 73:1117–1124). Since, as shown herein, the activity of src-family PTK is increased following infection with HIV, while not being bound by theory, we believe that the activity and levels of csk changes following infection with HIV to subsequently provide the observed increase in the activity of src-family PTK. The phosphotyrosine phosphatases CD45 and SHP-1 activate all src-family PTK by dephosphorylating the C-terminal negative regulatory tyrosine. (10). Since, as shown herein, the activity of src-family PTK is increased following infection with HIV, while not being bound by theory, we believe that the activity and levels of CD45 and PTPIC will change following infection with HIV to subsequently provide the observed increase in the activity of src-family PTK.

Another important aspect of the present invention is the use of plasma and/or serum media in the diagnosis of HIV infection by tyrosine kinase activity. In what we believe to be the first disclosure of PTK activity in extracellular fluids, we have identified more fyn-PTK activity in plasma from patients (n=5) infected with HIV as opposed to uninfected control (n=5). The use of plasma and/or serum to diagnose HIV infection precludes the need to process blood lysates and, thus, make the methods according to the present invention the most straightforward PTK assay known, to-date.

In a further aspect, the invention provides a method of assaying a specific enzyme signal transduction mediator present in a human body fluid characterized by the steps of:

(A) immobilizing an antibody to one or more of said enzymes plus a blocking agent, preferably a protein, preferably enolase, to a solid matrix, (B) exposing the immobilized antibody to a sample of said body fluid so as to achieve binding of said enzyme in said body fluid to form an immune complex, and effecting one or more of the treatments selected from the group consisting of (a)
  (i) exposing said immune complex to a mixture of ATP and labelled anti-phosphotyrosine antibody, wherein said label is chosen from an enzyme, fluorescent label, radioactive label and an avidin/biotin system employing any of these labels, so as to achieve tyrosine phosphorylation of said immune complex and said blockinig agent;
  (ii) binding of the labelled anti-phosphotyrosine to the phosporylated tyrosine; and
  (iii) measuring the amount of bound anti-phosphotyrosine antibody, (b)
  (i) exposing said immune complex to a mixture of tyrosine phosphorylated polypeptide and malachite green so as to achieve cleavage of phosphate from said phosphorylated tyrosine to provide free phosphate;
  (ii) reacting said free phosphate with malachite green so as to achieve a colour change; and
  (iii) measuring said colour change on a spectrophotometer; and (c)
  (i) exposing said immune complex to labelled antibodies specific for said bound enzyme in said immune complex, wherein said label is chosen from an enzyme, fluorescent label, radioactive label and an avidin/biotin system employing any of these labels, so as to achieve binding of the labelled antibody to the antigen;
  (ii) measuring the amount of bound labelled antibody, (C) comparing the level and activity of said enzyme signal transduction mediator obtained from treatments (a), (b) or (c) to a population standard of uninfected controls.

In a yet further aspect the invention provides a kit for assaying a specific enzyme signal transduction mediator present in a human body fluid said kit containing one or more reagents necessary for one or more of the steps as hereinbefore.

BRIEF DESCRIPTION OF THE DRAWINGS

In order that the invention may be better understood, preferred embodiments will now be described by way of example only with reference to the following drawings wherein.

DETAILED DESCRIPTION OF PREFERRED EMBODIMENTS

Figure 1:
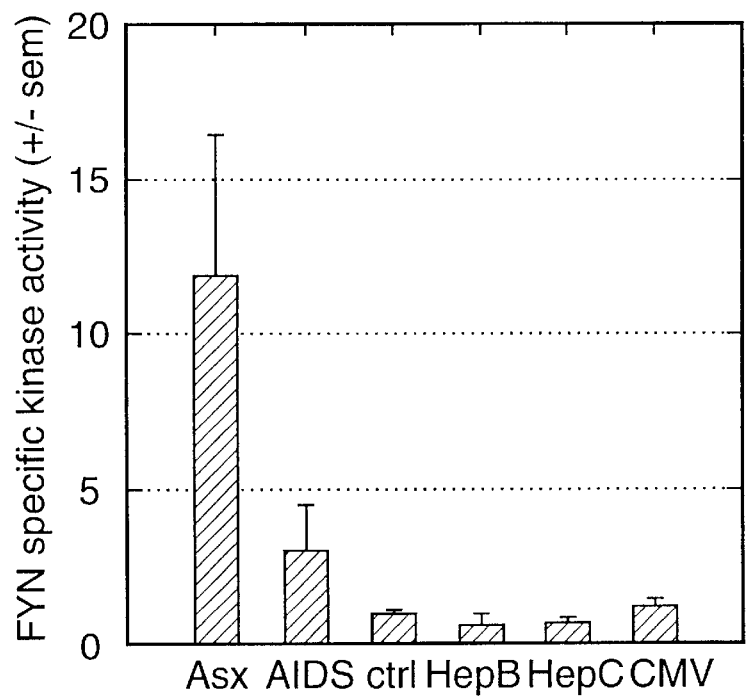
FIG. 1 is a chart of FYN tyrosine kinase activity from patients infected with HIV, Hepatitis B and C, cytomegalovirus (CMV) and uninfected controls.

Immune-complex kinase assay: Whole blood was obtained and PBMC isolated by density-gradient centrifugation using Ficoll-Hypaque. After washing, the isolated cells were lysed with cold RIPA lysis buffer (1% NP-40, 0.1% SDS, 0.1% Na deoxycholate, 50 mM HEPES, pH 7.3, 150 mM NaCl, 1 mM Na ortho-vanadate, 50 $\mu$M, $ZnCl_2$, 2 mM EDTA, 2 mM PMSF) at 4° C. The cell lysate was transferred to a 1.5 mL Eppendorf tube and centrifuged at 10,000 g for 10 minutes to remove particulate matter. The lysate was mixed with protein A-sepharose CL4B (Pharmacia) which had been previously complexed to anti-$p59^{fyn}$. The mixture was allowed to rotate at 4° C. for 1 hour to immunoprecipitate the protein of interest contained in the cell lysate. The immnunoprecipitate were washed 4 times with RIPA and an additional 4 times with kinase buffer (50 mM HEPES, pH 7.23, 150 mM NaCl, 1 mM $MgCl_2$, 1 mM $MnCl_2$, 0.5% NP-40). Each immunoprecipitate was then incubated with 5 $\mu$Ci of ($\gamma^{32}$P)ATP (ICN Biomedicals, Irvine, Calif.) in 20 $\mu$L of kinase buffer, with or without the addition of 2 $\mu$g of acid-treated enolase, at 37° C. for 10 minutes. After incubation with ($\gamma^{32}$P)ATP, reduced SDS-gel sample buffer was added to the reaction mixture and the samples boiled for 10 minutes. Samples were centrifuged at 10,000 g for 10 minutes and the supernatants $^{32}$P-labelled proteins were separated by SDS-polyacrylamide gel electrophoresis (PAGE) using gels containing 12% (vol/vol) polyacrylamide. The gel separated proteins were electrophoretically transferred to Immobilon filters (Millipore Corp., Bedford, Mass.), treated with 1M KOH at 56° for 2 hours to decrease by hydrolysis the amount of phosphoserine and phosphothreonine containing proteins, and then autoradiographed. The degree of phosphorylation of the enolase band was quantitated by densitometry.

Western blot analysis: Immobilon filters to which $^{32}$P-labelled proteins had been electrophoretically transferred (from kinase assay above) were blocked overnight with 5% skim milk powder in 10 mM Tris, 140 mM NaCl and 0.01% $NaN_3$, pH 8.2 (blocking solution). These blots were then incubated for one hour at 4° C. with a 1:250 dilution in blocking solution of a monoclonal anti-p59$^{fyn}$ (Transduction Labs). The blot was washed with TBS and goat anti-mouse IgG conjugate to horseradish peroxidase (GAM-HRP) was added at a final dilution of 1:2500 for one hour at 4° C. After washing with TBS the blot was developed by enhanced chemiluminescence (Amersham) and the intensity of the fyn band quantitated by densitometry.

Peripheral blood mononuclear cells (macrophages, B lymphocytes and T lymphocytes) were isolated from the blood of nine patients with asymptomatic HIV infection, average CD4 cell count 623±61 cells/µl. Lysates from 5×10$^6$ PBMC were immunoprecipitated with an antibody specific to p59$^{fyn}$ and the degree of kinase activity determined by in vitro immune complex kinase assay measuring the degree of phosphorylation of the exogeneous substrate enolase. The amount of fyn protein was determined by western blot. Both kinase activity and protein content were quantitated by densitometry and a ratio of kinase:protein determined and compared to that of 5×10$^6$ PBMC obtained from patients with AIDS (n=4), HIV uninfected control subjects (ctrl, n=34), from patients infected with hepatitis B virus (n=6), patients infected with hepatitis C virus (n=7) and patients infected with CMV (n=5).

Figure 5:
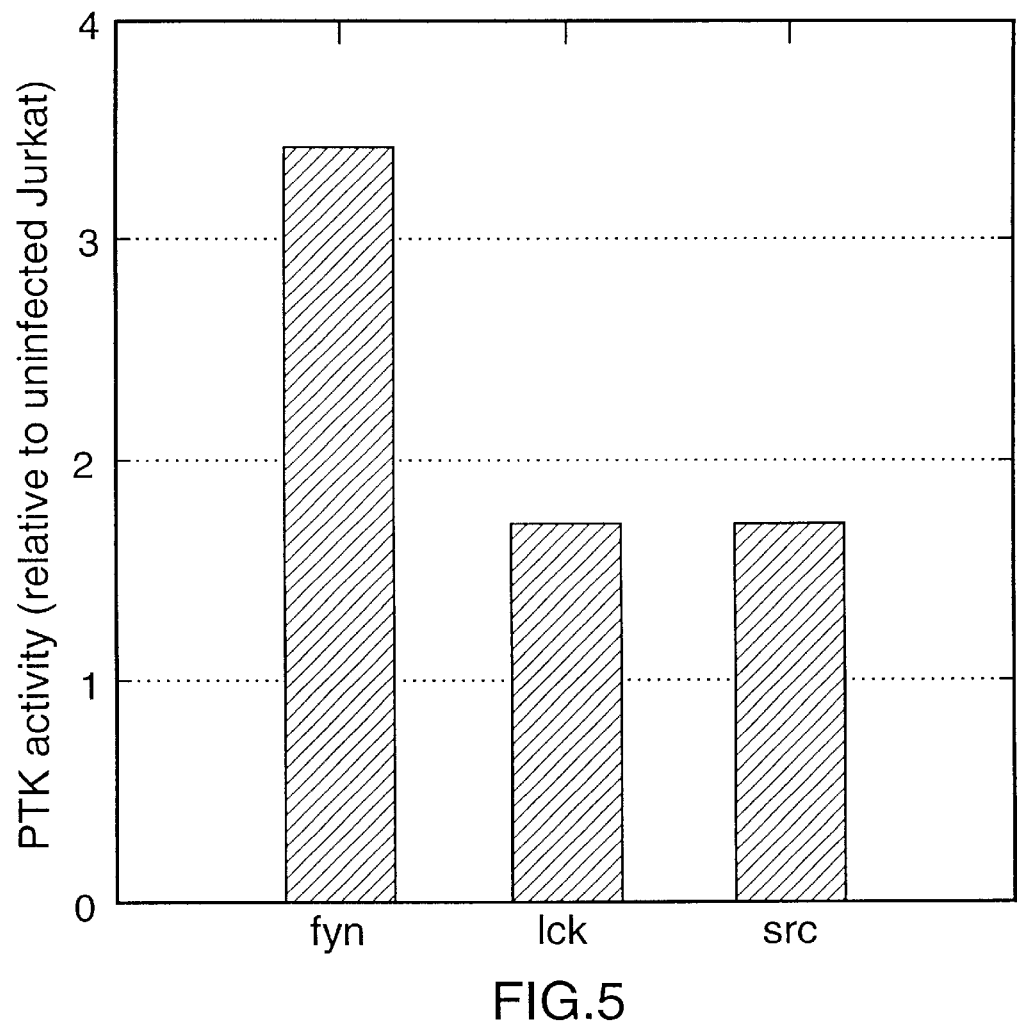
FIG. 5 is a chart showing the effect of HIV infection on the activity of src family kinases in Jurkat.

10$^7$ Jurkat (CD4-positive T cell line) were infected with HIV$_{IIIB}$ and harvested at various times following infection as indicated. Cells were lysed and lysates immunoprecipitated with an antibody for p59$^{fyn}$ and the degree of kinase activitiy determined by in vitro immune complex kinase assay. Kinase activity was quantitated by densitometry and compared to that of uninfected Jurkat. With reference to FIG. 5, this chart shows that HIV infection increases the activity of src family kinases in Jurkat. 10$^7$ Jurkat (−) or Jurkat infected with HIV for 24 hours (+) were lysed in RIPA lysis buffer. Kinase activity was determined by in vitro immune complex kinase assays of lysates immunoprecipitating with anti-lck, anti-fyn or anti-src antibody.

Figure 4:
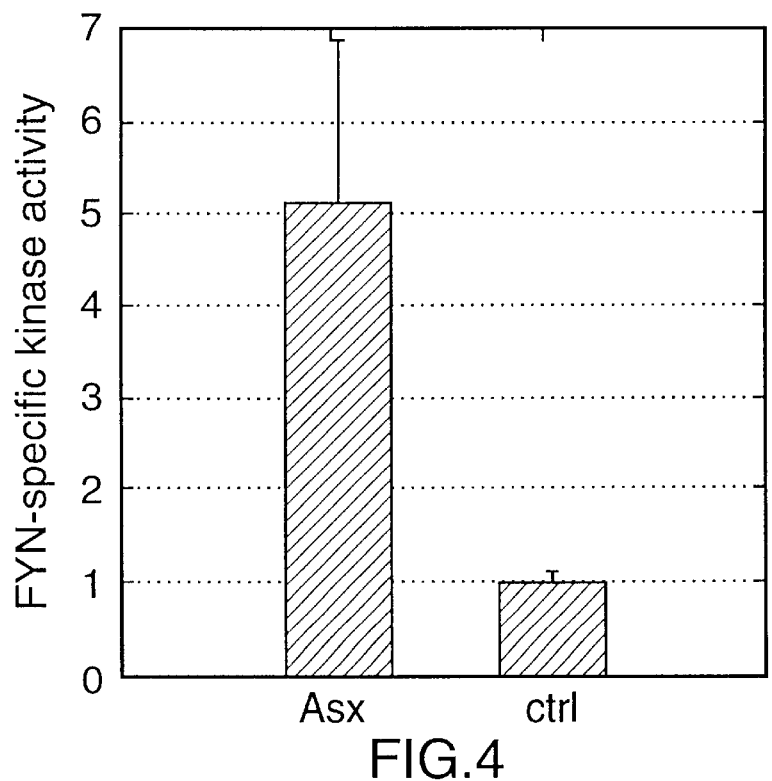
FIG. 4 is a chart of FYN activity in plasma of patients infected with asymptomatic HIV infection and uninfected controls.

With specific reference to FIG. 4, plasma was isolated from the blood of five patients with asymptomatic HIV infection (average CD4 cell count 623±61 cells/µl) and from 5 HIV uninfected controls. Plasma was pre-cleared of immunoglobulin by incubation with Protein A and the immunoglobulin-depleted plasma was immunoprecipitated with antibodies specific to p59$^{fyn}$ bound to protein A-sepharose. The degree of kinase activity was determined by in vitro immune complex kinase assay measuring the degree of phosphorylation (quantitated by densitometry) of the exogenous substrate enolase. The difference in mean kinase activity between asymptomatic patients and control subjects was statistically significant (p<0.05) as determined by an independent t test.

FIG. 5 illustrates that in vitro infection of a T cell line with HIV enhances the activity of all three PTKs tested. The activation of PTKs is regulated by kinases such as p50$^{csk}$ and phosphatases such as SHP-1 and CD45-associated phosphotoyrosine phosphatase, (10). Since HIV infection activates all three PTKs, HIV activates PTKs by activating a regulatory enzyme such as a phosphatase or kinase. Therefore, a change in activity of phosphatases, including CD45 and SHP-1, and kinases, including p56$^{lck}$, p59$^{fyn}$, p60$^{c-src}$ and p50$^{csk}$ is diagnostic of infection with HIV.

TABLE 1

| (A) STANDARD PTK | (B) UBI | (C) PIERCE |
|---|---|---|
| whole blood | whole blood | whole blood |
| Ficoll + wash | Ficoll + wash | Ficoll + wash |
| PBMC | PBMC | PBMC |
| lyse | lyse | lyse |

TABLE 1-continued

| (A) STANDARD PTK | (B) UBI | (C) PIERCE |
|---|---|---|
| ipt-immconj$^2$ | ipt-immconj$^2$ | ipt-immconj$^2$ |
| wash$^2$ | wash$^2$ | wash$^2$ |
| +ATP$^{(32)}$ | +ATP$^{(32)}$/peptide | +peptide |
| incubate | incubate | incubate |
| SDS-PAGE | count cpm | +anti-ptyr |
| transfer→NC | | +substrate |
| autoradiography | | read OD |
| densitometry$^1$ | | |
| NC→western blot | | |
| +anti-PTK | | |
| +anti-anti-PTK | | |
| ECL | | |
| densitometry$^1$ | | |
| ratio kinase:WB$^1$ | | |

Table 1 provides the steps in sequences of:
(A) an embodiment of the procedure of use in the present invention for determining enhanced protein tyrosine kinase activity; and
(B) and (C) being prior art detection test procedures currently available;
and wherein
$^1$provides semi-quantitative results;
$^2$the step is subject to investigator error The following methods provide instructions and exemplify, in more detail with reference to Table 1, how the practice of the invention may be effected.

Method A

1. Obtain whole blood by venepuncture.
2. Isolate PBMC by density gradient centrifugation.
3. Wash isolated PBMC 3 times with an isotonic solution.
4. Lyse PBMC with detergent based lysing buffer.
5. Centrifuge to remove particulate material.
6. Immunoprecipitate at 4° C. for at least 1 hour supernatant from step 5 above with previously prepared immuinoconjugates consisting of antibody to PTK bound to protein A-sepharose beads.
7. Wash immune complexes obtained from step 6 above 4 times with lysing buffer (from step 4 above).
8. Wash immune complexes from step 7 4 times with kinase buffer.
9. Add ($\gamma^{32}$P)ATP and enolase to immune complexes.
10. Incubate at 37° C. for 10 minutes.
11. Stop reaction by adding reduced SDS-sample buffer and boiling the sample for 10 minutes.
12. Centrifuge the sample for 10 minutes to remove particulate material.
13. Isolate protein of interest by SDS-PAGE (overnight).
14. Transfer separated proteins to nylon membrane by electrotransfer (5 hours).
15. Expose film to membrane (time varies).
16. Develop film.
17. Locate protein bands of interest.
18. Densitometry scan to semiquantitate kinase activity.
19. Place membrane into 5% skim milk to block (2 hours).
20. Western blot for total protein of interest using a monoclonal antibody (minimum of 2 hours or overnight).
21. Wash membrane and incubate with GAM-HRP (2 hours).
22. Wash membrane and do enhanced chemiluminescence and expose film to visualize protein of interest.
23. Do densitometry to semiquantitate the level of protein of interest 24. Calculate the ratio of kinase activity vs. the level of protein.

Method B

7. Wash immune-complexes 4 times and resuspend in dilution buffer.
8. Mix 5 μl of assay buffer stock solution, 5 μl of substrate peptide stock solution, and 10 μl of immunoprecipitates (from step 7 above) in polypropylene eppendorf tubes and keep mixture on ice. Use 5 μl of water instead of substrate peptide stock solution as a blank.
9. Start the reaction by addition of 5 μl (50 μCi) of ($\gamma^{32}$P)ATP and incubate the reaction mixture at 30° C. for a maximum of 30 minutes.
10. Stop the reaction by addition of 10 μl of 50% acetic acid.
11. Centrifuge sample for 5 minutes.
12. Spot 25 μl of the supernate from each test and blank onto a 1.5 cm×1.5 cm p81 phosphocellulose filter paper disc.
13. Wash the filter paper discs 4 times with excess phosphoric acid and once with excess acetone.
14. Allow discs to dry.
15. Put discs into scintillation vials and measure radioactivity on a scintillation counter.

Method C

Steps 1–6 are identical to Methods A and B.

7. Wash immunoprecipitate 4 times with reaction buffer.
8. Previous to or concurrently with Steps 1–7, add the appropriate biotinylated tyrosine kinase substrate peptide to NeutrAvidin-coated pre-blocked microwell strips.
9. Wash strip with washing buffer.
10. Add immune complexes from 7 above and nonradioactive ATP.
11. Allow reaction to proceed. The peptide substrate will become phosphorylated on tyrosine residues.
12. Wash strip with washing buffer.
13. Add HRP-labeled anti-phosphotyrosine antibody.
14. Allow antibody to bind to phosphotyrosine-containing residues.
15. Wash strip and develop any bound HRP by a colorimetric substrate 1-step™ Turbo TMB.
16. Measure optical density at 450 nm using a spectrophotometer.

TABLE 2

ENZYME SIGNAL TRANSDUCTION MEDIATOR ASSAYS

1. Conjugate antibody to solid support
2. Block unbound site with blocking agent, preferably a protein, preferably enolase
3. Add test sample (body fluid) to capture enzyme of choice
4. Wash

| Kinase[1] | Phosphatase[2] | Protein[3] |
|---|---|---|
| 5. add ATP + labelled antibody[4] | 5. add ptyr-containing peptide + malachite green | 5. add labelled anti-enzyme antibody[4] |
| 6. wash | 6. read coloured product | 6. wash |
| 7. add reagent to detect anti-ptyr antibody | | 7. add reagent to detect labelled antibody |
| 8. read results | | 8. read results |

NOTES:
[1]This assay detects kinase activity
[2]This assay detects phosphatase activity
[3]This assay detects protein levels of the enzymes
[4]Label could be enzyme, fluorescent, radioactive or a biotin/avidin conjugate system employing any of these labels.

Table 2 shows the general steps involving preferred methods of enzyme signal transduction mediator assays according to the invention by assaying the activities or protein levels of kinases and phosphatases.

By the term blocking agent is meant a compound that blocks those sites left unconjugated following binding of an antibody to a solid matrix support. During conjugation of an antibody to a solid matrix, not all matrix sites are coated with antibody. A blocking agent is used to block these unconjugated matrix sites in order to prevent non-specific binding of substances in the test sample to be subsequently applied. The blocking agent is a compound, preferably a protein, more preferably a substrate for an enzyme signal transduction mediator, and yet more preferably, an enolase.

Enzyme protein levels are also measured, since levels of FYN protein are reduced in the cells of patients infected with HIV (FIG. 3), in contrast to the kinase activity of FYN, which is increased. Also, in contrast to reduced levels of intracellular kinase proteins, the FYN kinase protein in plasma and serum of patients infected with HIV is increased due to the increased turnover of blood cells. Lymphocytes of patients infected with HIV have a much shorter half-life than those of patients uninfected due to HIV cytolytic effects (18, 19). Since these infected lymphocytes are lysing and depositing their intracellular contents, including active kinases and phosphatases into plasma, the levels of enzyme protein as well as enzyme activity is elevated in plasma. Enzyme activity is elevated in plasma.

With reference to Table 2, if the enzyme is a kinase, following immunoprecipitation of the kinase, kinase activity is detected by adding a combination of 0.25 umol ATP and 1.0 ug labeled anti-phosphotyrosine antibody in warm kinase buffer and incubating for 10 minutes. This label may be an enzyme, fluorescent, radioactive or an avidin/biotin system employing these labels. Excess ATP and anti-phosphotyrosine antibody are washed off and, in the case of an enzyme, the appropriate substrate is added. The results are read on the appropriate detection monitor, e.g. spectrophotometer, fluorimeter or scintillation counter.

If the enzyme is a phosphatase, following immunoprecipitation of the phosphatase, phosphatase activity is detected by adding a mixture of tyrosine phosphorylated polypeptide and malachite green and incubating for 10 minutes. Colour change of malachite green by detecting free phosphate cleaved from phosphotyrosine, is assessed by reading the plate/bead at 650–660 nm.

To detect levels of enzyme protein, a standard ELISA technique is employed. Following immunoprecipitation, the enzyme is detected by incubating with a labeled secondary antibody specific for the enzyme. The labels and their methods of detection are described hereinabove.

Figure 6:
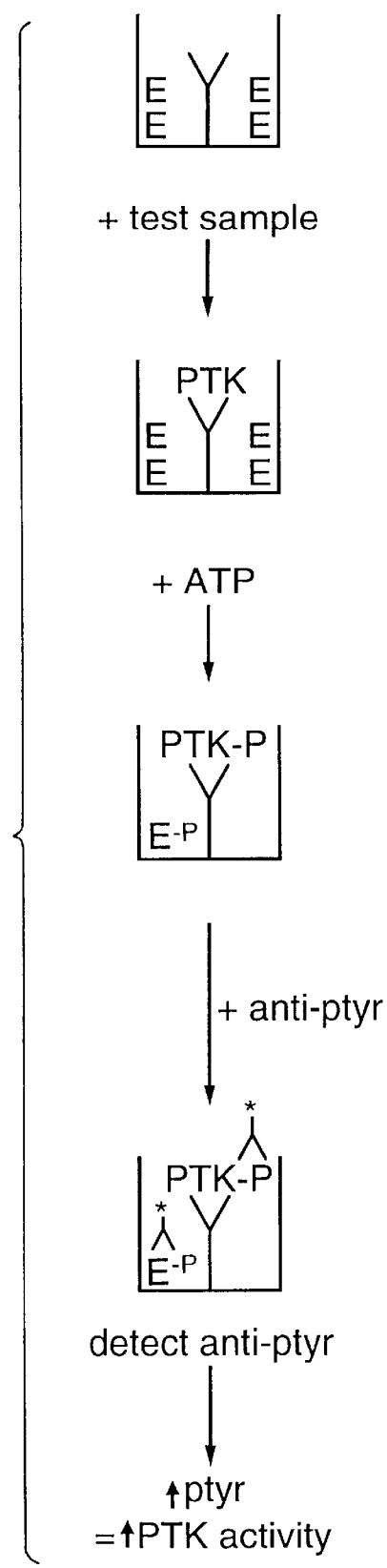
FIG. 6 represents a pictorial representation of an immuno assay according to the invention.

Reference is made to FIG. 6 wherein

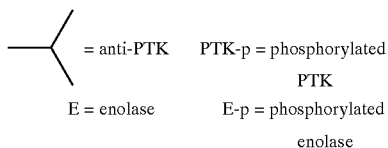

in a 96-well assay.

Quantitative Kinase Assay.

This technique is based on standard ELISA techniques as described. Anti-enzyme is conjugated to a polystyrene microtitre plate or bead by suspending the antibody in 0.1 M carbonate buffer, pH 9.6 and incubating with polystyrene solid support overnight at room temperature to bind antibody to the well. Following binding of anti-fyn, the wells are washed in carbonate buffer and unbound sites blocked by addition of Enolase to take advantage of enolase as both a blocking agent and as an exogenous substrate for kinase activity. Fyn is immunoprecipitated from the test sample by incubating 200 μl sample in wells for 1 hour at 4° C.

Test samples. Plasma and/or serum may be used in either the 96-well plate assay or the bead assay. Whole blood lysates are prepared by mixing a 10×RIPA solution at a 1:10 dilution in whole blood and used as a test sample for the bead assay. PBMC, prepared using the PCT Vacutainer tube available from Becton Dickinson, is lysed in RIPA and used as a test sample for the 96-well plate assay. Also urine or saliva may be used in either assay.

Fyn kinase activity was determined in plasma as follows.

1.0 ml plasma (separated from heparinized venous blood) was first incubated with a slurry of Staphylococcus aureus containing cell surface protein A to remove much of the immunoglobulin present in plasma. The immunoglobulin-depleted plasma was immunoprecipitated with anti-fyn and kinase assays performed in the presence of enolase to determine levels of fyn kinase activity. Fyn kinase was analyzed by densitometry to determine kinase activity. The data shown in FIG. 4 represents 5 individuals from each patient group studied, i.e. Asx=asymptomatic HIV infection; ctrl=uninfected control.

FIG. 1 shows that FYN tyrosine kinase activity was elevated in patients infected with HIV, but not in patients infected with Hepatitis B and C virus, CMV or control.

Peripheral blood mononuclear cells (macrophages, B lymphocytes and T lymphocytes) were isolated from the blood of nine patients with asymptomatic HIV infection (average CD4 cell count 623±61 cells/μl) and from four patients with AIDS (average CD4 cell count 15±4 cells/μl). Lysates from 5×10$^6$ PBMC were immunoprecipitated with antibodies specific to 59$^{fyn}$ and the degree of kinase activity determined by in vitro immune complex kinase assay measuring the degree of phosphorylation of the exogenous substrate enolase. The amount of fyn protein was determined by western blot. Both kinase activity and protein content were quantitated by densitometry, FYN specific kinase activity (ratio of kinase activity:kinase protein) determined and compared to that of 5×10$^6$ PBMC obtained from HIV uninfected control subjects (ctrl, n=34), patients infected with Hepatitis B virus (n=6) or Hepatitis C virus (n=7) or patients testing seropositive to cytomegalovirus (CMV, n=5). The difference in mean kinase activity between asymptomatic patients and control subjects (p=1.320×10$^{-5}$) and between AIDS patients and control subjects (p=9.366× 10$^{-5}$) was statistically significant as determined by an independent t test.

Figure 2:
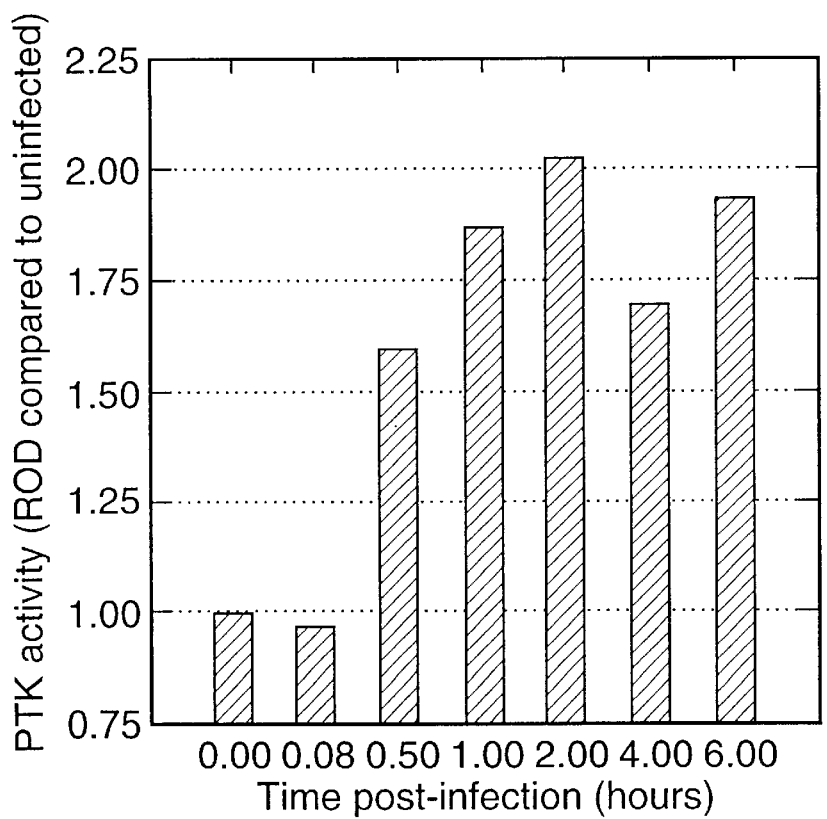
FIG. 2 is a chart of FYN PTK activity against time after in vitro HIV infection.

FIG. 2 shows that infection of a human CD4-positive T cell line with HIV in vitro elevates protein tyrosine kinase activity within 30 minutes of infection.

Figure 3:
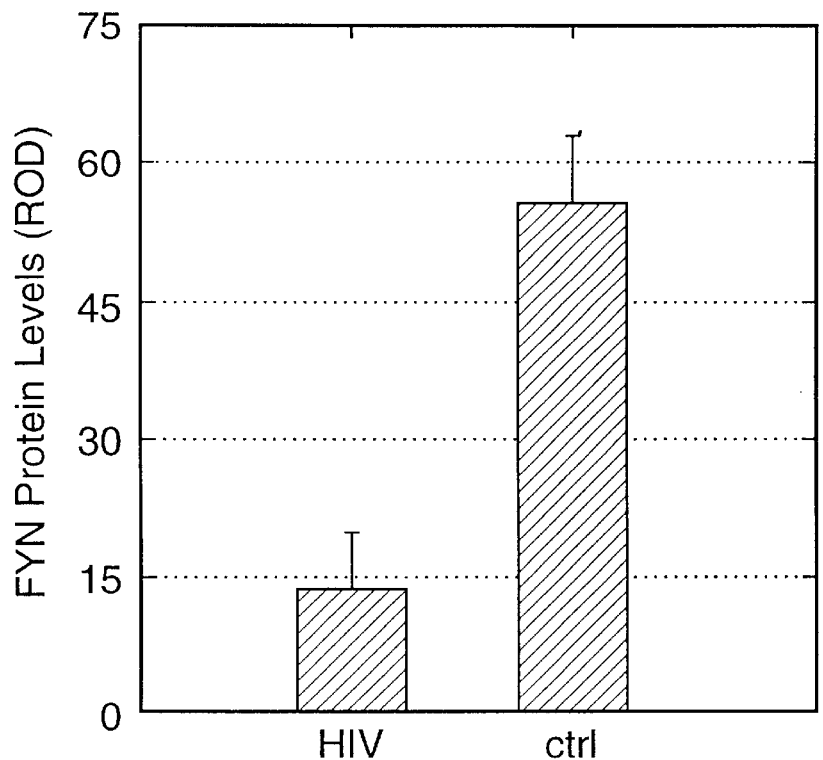
FIG. 3 is a chart of FYN protein levels in patients infected with HIV and uninfected controls.

FIG. 3 shows that infection with HIV in vivo decreases levels of protein tyrosine kinase.

While the invention has been described in detail and with reference to specific embodiments thereof, it will be apparent to one skilled in the art that various changes and modifications can be made therein without departing from the spirit and scope of the invention.

We claim:

1. A method for the detection of HIV infection comprising detecting a change in signal transduction mediator activity or level in a body fluid relative to an HIV uninfected population standard.

2. A method as defined in claim 1 wherein said change is an increase.

3. A method as defined in claim 1 wherein said change is a decrease.

4. A method as defined in claim 1 wherein said mediator is a kinase.

5. A method as defined in claim 1 wherein said mediator is a phosphatase.

6. A method as defined in claim 4 wherein said kinase is selected from a tyrosine kinase, a serine-threonine kinase, a tyrosine-threonine kinase and a tyrosine-serine-threonine kinase.

7. A method as defined in claim 6 wherein said mediator is the src-family of tyrosine kinases.

8. A method as defined in claim 6 wherein said mediator is the csk-family of tyrosine kinases.

9. A method as defined in claim 7 wherein said mediator is selected from src, yes, fyn (p59$^{fyn}$) lck (p56$^{lck}$), fgr, hck, blk, and yrk.

10. A method as defined in claim 1 wherein said body fluid is selected from serum, plasma, saliva, urine and blood cell lysate.

* * * * *